(12) United States Patent
Nakamura et al.

(10) Patent No.: US 10,683,253 B2
(45) Date of Patent: Jun. 16, 2020

(54) METHOD FOR PRODUCING HIGH-PURITY TEREPHTHALIC ACID

(71) Applicant: Mitsubishi Gas Chemical Company, Inc., Chiyoda-ku (JP)

(72) Inventors: Goh Nakamura, Kurashiki (JP); Hideaki Fujita, Kurashiki (JP); Kotaro Murakami, Kurashiki (JP); Ryusuke Shigematsu, Chiyoda-ku (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/331,851

(22) PCT Filed: Aug. 28, 2017

(86) PCT No.: PCT/JP2017/030795
§ 371 (c)(1),
(2) Date: Mar. 8, 2019

(87) PCT Pub. No.: WO2018/051775
PCT Pub. Date: Mar. 22, 2018

(65) Prior Publication Data
US 2019/0233361 A1 Aug. 1, 2019

(30) Foreign Application Priority Data
Sep. 14, 2016 (JP) .................... 2016-179404

(51) Int. Cl.
*C07C 51/47* (2006.01)
*C07C 63/26* (2006.01)
(Continued)

(52) U.S. Cl.
CPC ............ *C07C 51/47* (2013.01); *B01D 9/0059* (2013.01); *C07C 51/43* (2013.01); *C07C 63/26* (2013.01);
(Continued)

(58) Field of Classification Search
CPC ....... C07C 51/43; C07C 51/47; C07C 51/215; C07C 63/26; C07B 2200/13; B01D 9/0059; B01D 2009/009
See application file for complete search history.

(56) References Cited

U.S. PATENT DOCUMENTS 5,567,842 A * 10/1996 Izumisawa .............. C07C 51/43
562/486
6,034,269 A 3/2000 Turner et al.
(Continued)

FOREIGN PATENT DOCUMENTS

JP 55-87744 A 7/1980
JP 57-53431 A 3/1982
(Continued)

OTHER PUBLICATIONS

International Search Report dated Sep. 26, 2017 in PCT/JP2017/030795 filed Aug. 28, 2017.

*Primary Examiner* — Yate' K Cutliff
(74) *Attorney, Agent, or Firm* — Oblon, McClelland, Maier & Neustadt, L.L.P.

(57) ABSTRACT

Disclosed herein is a method for producing high-purity terephthalic acid, including steps of dissolving crude terephthalic acid crystal in water and performing catalytic hydrogenation treatment, depressurizing and cooling a reaction liquid after the catalytic hydrogenation treatment in stages with two or more stages of crystallization vessels, to crystallize terephthalic acid to obtain a terephthalic acid slurry, introducing the terephthalic acid slurry into an upper portion of a mother liquor replacement tower, bringing the terephthalic acid crystal into contact with an upward flow of replacement water introduced from a tower lower compartment of the mother liquor replacement tower while making the terephthalic acid crystal settled down in the tower, withdrawing the terephthalic acid crystal as slurry with the (Continued)

replacement water from the tower lower compartment, subjecting the slurry withdrawn from the tower lower compartment to solid-liquid separation into water and the terephthalic acid crystal, and drying the separated terephthalic acid crystal.

4 Claims, 1 Drawing Sheet

(51) Int. Cl.
    *B01D 9/00*     (2006.01)
    *C07C 51/43*     (2006.01)
    *C07C 51/215*     (2006.01)

(52) U.S. Cl.
    CPC ...... *B01D 2009/009* (2013.01); *C07C 51/215* (2013.01)

(56) References Cited

U.S. PATENT DOCUMENTS

| | | | |
|---|---|---|---|
| 7,262,323 B2 * | 8/2007 | Fujita | ............ C07C 51/47 422/31 |
| 2015/0361028 A1 | 12/2015 | Grolman | |

FOREIGN PATENT DOCUMENTS

| | | |
|---|---|---|
| JP | 7-291896 A | 11/1995 |
| JP | 8-225489 A | 9/1996 |
| JP | 8-231465 A | 9/1996 |
| JP | 10-195016 | 7/1998 |
| JP | 11-228492 A | 8/1999 |
| JP | 2002-522406 A | 7/2002 |
| JP | 2006-96710 A | 4/2006 |
| JP | 2009-203163 A | 9/2009 |
| JP | 2014-524928 A | 9/2014 |

* cited by examiner

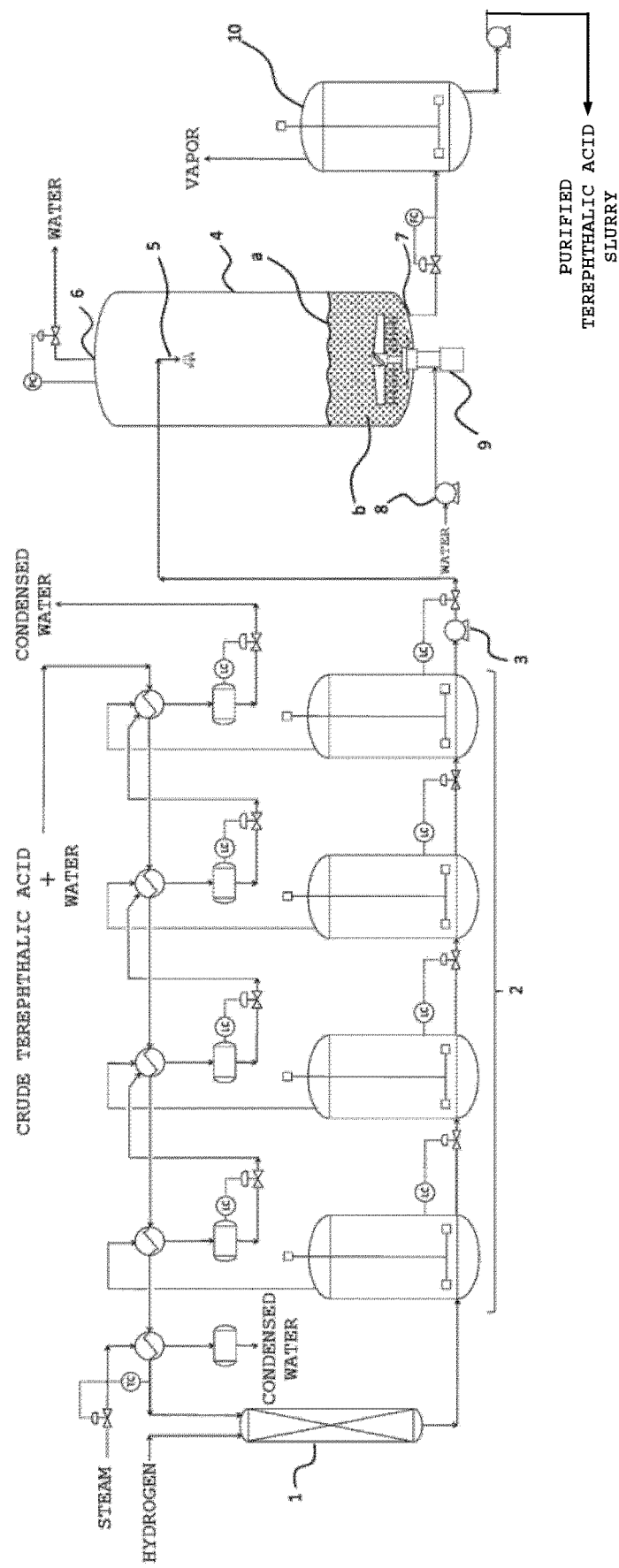

METHOD FOR PRODUCING HIGH-PURITY TEREPHTHALIC ACID

CROSS-REFERENCE TO RELATED APPLICATIONS

This application is a National Phase of PCT/JP2017/030795, which was filed on Aug. 28, 2017. This application is based upon and claims the benefits of priority to JP 2016-179404, which was filed on Sep. 14, 2016.

TECHNICAL FIELD

The present invention relates to a method for producing high-purity terephthalic acid.

BACKGROUND ART

Terephthalic acid is produced by the liquid-phase oxidation reaction of a p-phenylene compound such as p-alkyl-benzenes including p-xylene as a representative example. Usually, in the production of terephthalic acid, a catalyst such as cobalt or manganese is used, or a catalyst obtained by adding an accelerant such as a bromine compound or acetaldehyde to a catalyst such as cobalt or manganese is used, with acetic acid as a solvent.

However, in this liquid-phase oxidation reaction, acetic acid is used as the solvent, the obtained crude terephthalic acid slurry includes, in large amounts, impurities such as 4-carboxybenzaldehyde (hereinafter also described as 4CBA), para-toluic acid (hereinafter also described as p-TOL), and benzoic acid, or other various coloring impurities. The crude terephthalic acid obtained by separating from the crude terephthalic acid slurry also includes these impurities as mixed therein, and thus a considerably higher purification technique is required for the purpose of obtaining high-purity terephthalic acid.

As a method for purifying crude terephthalic acid, there have been known various methods such as dissolving crude terephthalic acid in acetic acid or water, a mixed solvent thereof, or the like at high temperature and high pressure followed by catalytic hydrogenation treatment, decarbonylation treatment, oxidation treatment, or recrystallization treatment, or high temperature immersion treatment in a slurry condition in which terephthalic acid crystals are partially dissolved. When any purification method is used, finally, the operation of separating the terephthalic acid crystals from the mother liquor is required.

Oxidation intermediates such as 4CBA, p-TOL, and benzoic acid or coloring substances which are present as impurities in the oxidation-derived slurry or the slurry resulting from purification of crude terephthalic acid are dissolved in the dispersion medium of the slurry at high temperature. Thus, when the slurry is cooled to around 100° C. to give slurry containing terephthalic acid crystals, these impurities are incorporated in the terephthalic acid crystals, with the result that it is difficult to obtain high-purity terephthalic acid.

Therefore, in order to obtain high-purity terephthalic acid from slurry after the purification treatment of crude terephthalic acid, it is necessary to separate the terephthalic acid from the mother liquor under the conditions of high temperature and high pressure. The method most generally used as a method for separating a mother liquor from slurry comprising terephthalic acid crystals is a centrifugation method. The centrifugation method is a method in which the slurry is introduced into a basket rotating at high speed so as to cause the dispersion medium to overflow from the top of the basket while directing the crystals to the bottom of the basket. It is known that the centrifugation method involves some difficulties in continuous operation at high temperature and high pressure because of the structural and functional restrictions of the centrifuge.

First, the crystals are difficult to rinse during the centrifugation or after the separation, and thus the amount of the dispersion medium adhered to the crystals tends to increase. A common method employed to solve this problem is to form a cake of the centrifugally separated terephthalic acid crystals into slurry with a fresh, hot solvent. This method, however, has the disadvantage of requiring several repetitions of the separation procedure. Further, since high speed rotation is performed at high temperature and high pressure, the maintenance and service of the centrifuge are complicated and difficult, and investment in them increases, and it is difficult to say that the centrifugation method is advanced as a technique in this field.

As a separation technique alternative to the centrifugation, a mother liquor replacement apparatus making use of gravitational sedimentation of terephthalic acid crystals has been proposed. For example, in Patent Literature 1, a mother liquor replacement apparatus within which a lateral plate with a plurality of holes is provided is disclosed, and it is described that when the mother liquor replacement apparatus does not have such a structure, the efficiency of replacement decreases due to the channeling or back mixing of the fluid in the apparatus. In addition, in Patent Literature 2, it is described that by providing in an apparatus a shelf plate forming a slope, the replacement performance improves.

In addition, a mother liquor replacement apparatus requiring no shelf plates is also proposed. Patent Literature 3 describes a dispersion medium replacement apparatus having a simple structure that does not require a shelf plate, characterized in that in a dispersion medium replacement tower in which a terephthalic acid slurry and a dispersion medium for replacement are introduced from the upper portion of the tower and the lower portion of the tower respectively, and the terephthalic acid crystals settling in the tower and the dispersion medium for replacement rising in the tower are brought into contact with each other in a counterflow, a stirring apparatus is provided in the lower portion of the tower, and further the terephthalic acid content in the slurry in the lower portion region is made higher than the terephthalic acid content in the slurry in the middle part region.

Regarding a method for producing purified terephthalic acid without a mother liquor replacement step, Patent Literature 4 describes a process in which crude terephthalic acid is dissolved in water and brought into contact with hydrogen in the presence of a catalyst of a platinum group metal for reduction treatment, this treatment liquid is crystallized to form slurry, and the crystals in the above slurry are separated by a solid-liquid separation apparatus to obtain purified terephthalic acid. It is disclosed that the water content of the dehydrated cake of terephthalic acid obtained by the solid-liquid separation in this process based on the terephthalic acid is 15 to 20% by mass, and when drying is further performed using a fluidized bed dryer, the step of decreasing the water content of the terephthalic acid to 14% by mass or less by a method such as flash drying, pre-drying by a heater, or mixing dry terephthalic acid is necessary. Patent Literature 4 discloses that various solid-liquid separation methods such as a screen bowl type centrifuge, a rotary vacuum filter, and a horizontal belt filter are attempted, but it is difficult to decrease the water content to 14% by mass or less only by solid-liquid separation.

Meanwhile, terephthalic acid is reacted with ethylene glycol or the like and mainly used as a starting material of polyester. When such large particle diameter particles that the particle diameter of terephthalic acid exceeds 200 μm increase too much, the terephthalic acid is likely to remain as an unreacted component, and as a result, the need to increase reaction time arises, and the problem of the increase of by-products arises.

Patent Literature 5 discloses a method for setting the proportion of particle diameters exceeding 210 μm at 10% by mass or less. In the method in Patent Literature 5, the proportion of particle diameters exceeding 210 μm is set at 10% by mass or less by defining crystallization temperature in a first crystallization vessel and the range of the stirring power of a stirring blade when dissolving crude terephthalic acid in an aqueous medium, subjecting the solution to catalytic hydrogenation treatment with a platinum group metal catalyst, and performing cooling in stages in multiple stages of crystallization vessels connected in series for crystallization.

CITATION LIST

Patent Literature

Patent Literature 1: Japanese Unexamined Patent Application Publication No. 57-053431
Patent Literature 2: Japanese Unexamined Patent Application Publication No. 55-087744
Patent Literature 3: Japanese Unexamined Patent Application Publication No. 8-231465
Patent Literature 4: Japanese Unexamined Patent Application Publication No. 2009-203163
Patent Literature 5: Japanese Unexamined Patent Application Publication No. 08-225489

SUMMARY OF INVENTION

Technical Problem

It is an object of the present invention to provide a method for producing high-purity terephthalic acid, comprising the steps of performing crystallization after the catalytic hydrogenation treatment of a crude terephthalic-acid-containing liquid obtained by liquid-phase oxidation, further replacing the terephthalic acid crystal slurry by a purified terephthalic acid slurry of clean water by a mother liquor replacement apparatus, and further performing solid-liquid separation and drying, in which mother liquor replacement is efficiently performed, the heating load during the step of drying the purified terephthalic acid cake after the solid-liquid separation is small, and the high-purity terephthalic acid exhibits good behavior as a starting material of polyester.

Solution to Problem

The present inventors have studied diligently over and over and as a result found a method in which mother liquor replacement is efficiently performed, the heating load during purified terephthalic acid cake drying after solid-liquid separation is small, and high-purity terephthalic acid that exhibits good behavior as a starting material of polyester is produced, by operating a crystallization step and a mother liquor replacement step after the catalytic hydrogenation treatment of a crude terephthalic-acid-containing liquid under particular conditions, leading to the completion of the present invention.

Specifically, the present invention is as follows.

[1]

A method for producing high-purity terephthalic acid, comprising following steps (a) to (e):
(a) a step of obtaining a crude terephthalic acid crystal by liquid-phase oxidizing a p-phenylene compound,
(b) a step of dissolving the crude terephthalic acid crystal in water and then subjecting to catalytic hydrogenation treatment,
(c) a step of depressurizing and cooling a reaction liquid after the catalytic hydrogenation treatment in stages with two or more stages of crystallization vessels, to crystallize terephthalic acid to obtain a terephthalic acid slurry,
(d) a step of introducing the terephthalic acid slurry into an upper portion of a mother liquor replacement tower, bringing the terephthalic acid crystal into contact with an upward flow of replacement water introduced from a tower bottom portion of the mother liquor replacement tower while making the terephthalic acid crystal settled down in the tower, and withdrawing the terephthalic acid crystal as slurry with the replacement water from the tower lower compartment, and
(e) a step of subjecting the slurry withdrawn from the tower lower compartment to solid-liquid separation into water and the terephthalic acid crystal, and drying the separated terephthalic acid crystal, wherein
when a throughput of the crystal subjected to the catalytic hydrogenation treatment is Q [ton/hr], and residence time in a first-stage crystallization vessel of the two or more stages of crystallization vessels is $T_1$ [hr], and a cross-sectional area of the mother liquor replacement tower is A [m$^2$], following conditions (1) to (3):

$$0.07 \leq T_1 \leq 0.5 \quad (1)$$

$$0.3 \leq A/Q \leq 0.8 \quad (2)$$

$$0.035 \leq T_1 \times A/Q \leq 0.25 \quad (3)$$

are all satisfied.
[2]
The production method according to [1], wherein number of stages of the two or more stages of crystallization vessels is three to five stages.
[3]
A high-purity terephthalic acid wherein
a median diameter is 100 to 130 μm,
a proportion of a crystal having particle a diameter of less than 53 μm is 15% or less, and
a proportion of a crystal having particle a diameter of 212 μm or more is 15% or less.
[4]
The high-purity terephthalic acid according to [3], wherein a proportion of a crystal having a particle diameter of less than 38 μm is 7% or less.

Advantageous Effects of Invention

According to the present invention, in the production of high-purity terephthalic acid using a mother liquor replacement tower, mother liquor replacement is efficiently performed, the heating load during the step of drying a purified terephthalic acid cake after solid-liquid separation is small, and purified terephthalic acid that exhibits good behavior as a starting material of polyester can be produced.

BRIEF DESCRIPTION OF DRAWING

FIG. 1 shows a schematic view of a terephthalic acid purification process used in Examples.

DESCRIPTION OF EMBODIMENTS

A mode for carrying out the present invention (hereinafter simply referred to as "present embodiment") will be described in detail below. The present embodiment below is an illustration for describing the present invention and is not intended to limit the present invention to the following contents. Appropriate modifications can be made to the present invention without departing from the spirit thereof.

The method for producing high-purity terephthalic acid in the present embodiment comprises following steps (a) to (e):

(a) a step of obtaining a crude terephthalic acid crystal by liquid-phase oxidizing a p-phenylene compound,
(b) a step of dissolving the crude terephthalic acid crystal in water and then subjecting to catalytic hydrogenation treatment,
(c) a step of depressurizing and cooling a reaction liquid after the catalytic hydrogenation treatment in stages with two or more stages of crystallization vessels, to crystallize terephthalic acid to obtain a terephthalic acid slurry,
(d) a step of introducing the terephthalic acid slurry into an upper portion of a mother liquor replacement tower, bringing the terephthalic acid crystal into contact with an upward flow of replacement water introduced from a tower bottom portion of the mother liquor replacement tower while making the terephthalic acid crystal settled down in the tower, and withdrawing the terephthalic acid crystal as slurry with the replacement water from the tower lower compartment, and
(e) a step of subjecting the slurry withdrawn from the tower lower compartment to solid-liquid separation into water and the terephthalic acid crystal, and drying the separated terephthalic acid crystal.

In the method for producing high-purity terephthalic acid in the present embodiment, when the throughput of the crystal subjected to the catalytic hydrogenation treatment is Q [ton/hr], and the residence time in the first-stage crystallization vessel of the two or more stages of crystallization vessels is $T_1$ [hr], and the cross-sectional area of the mother liquor replacement tower is A [m$^2$], following conditions (1) to (3):

$$0.07 \leq T_1 \leq 0.5 \quad (1)$$

$$0.3 \leq A/Q \leq 0.8 \quad (2)$$

$$0.035 \leq T_1 \times A/Q \leq 0.25 \quad (3)$$

are all satisfied.

The high-purity terephthalic acid in the production method in the present embodiment refers to terephthalic acid purified through the above steps (a) to (e) (hereinafter also referred to as purified terephthalic acid). The purified terephthalic acid in the present embodiment is preferably in the form of crystal.

[Step (a)]

The step (a) is the step of obtaining a crude terephthalic acid crystal by liquid-phase oxidizing a p-phenylene compound.

The step (a) is preferably the step of subjecting a p-phenylene compound to liquid-phase oxidation followed by depressurization and cooling to obtain a crude terephthalic acid slurry, and separating the reaction mother liquor from the obtained crude terephthalic acid slurry to obtain a crude terephthalic acid crystal.

The p-phenylene compound in the present embodiment has on phenyl two carboxyl groups or oxidizable substituents that can produce carboxyl groups by liquid-phase air oxidation, and the above two carboxyl groups or oxidizable substituents are in para positions as a positional relationship.

Examples of the oxidizable substituent include a methyl group, an ethyl group, a propyl group, an isopropyl group, an aldehyde group, and an acetyl group. The two substituents on the phenyl may be the same or different from each other.

As the oxidant used in the liquid-phase oxidation, oxygen or air is used, and the oxidant is not limited to either of them. In the case of oxidation in an acetic acid solution in the presence of cobalt and manganese catalysts and a bromide compound as a co-catalyst, air is sufficient. When the oxidation is carried out in an acetic acid solution in the presence of a cobalt catalyst, oxygen is preferably used.

When cobalt and manganese catalysts are used as the catalyst, it is preferable to further use a bromine compound. Bromine compounds are generally considered to act as co-catalysts, and hydrogen bromide or sodium bromide is preferred.

When a cobalt catalyst is used, it is preferable to further use acetaldehyde, methyl ethyl ketone, or the like as a promoter.

The crude terephthalic acid crystal obtained by a liquid-phase oxidation reaction in an acetic acid solution generally contains many impurities such as 4CBA, and the value of OD340, which is a measure of whiteness, of the crude terephthalic acids is not sufficient for it to be used by itself as a polymer material. In the present embodiment, there is no particular upper limit to the content of 4CBA and other impurities in the crude terephthalic acid crystal. Similarly, there is no particular upper limit to OD340. When the conditions in the liquid-phase oxidation step are set to such conditions that the 4CBA content in the crude terephthalic acid crystal is 500 ppm or more, the combustion loss of acetic acid due to the oxidation reaction tends to be able to be suppressed.

[Step (b)]

The step (b) is the step of subjecting the crude terephthalic acid crystal to catalytic hydrogenation treatment.

The step (b) is preferably the step of dissolving the crude terephthalic acid crystal in water at high temperature and high pressure and then subjecting the solution to catalytic hydrogenation treatment.

In the production method in the present embodiment, the crude terephthalic acid crystal is mixed with water and subjected to the catalytic hydrogenation treatment. This catalytic hydrogenation treatment is carried out under high temperature and high pressure conditions in order to be carried out in a solution state. The catalytic hydrogenation treatment is performing a catalytic hydrogenation reaction.

The temperature of the catalytic hydrogenation reaction is preferably 260° C. or more, more preferably 270 to 300° C.

The concentration of crude terephthalic acid in the solution is preferably 10 to 40% by mass.

The pressure of the catalytic hydrogenation reaction is not particularly limited as long as it is a pressure which is sufficient for the solution containing terephthalic acid to maintain the liquid-phase and at which hydrogen partial pressure suitable for the catalytic hydrogenation reaction can be maintained. The pressure of the catalytic hydrogenation reaction is generally preferably 6 to 10 MPa.

A group VIII noble metal is used as the catalyst used for the catalytic hydrogenation reaction. The group VIII noble metal is preferably palladium, platinum, ruthenium, and rhodium, more preferably palladium and platinum. These metals need not necessarily be used singly, and two or more of these metals may be used in combination if necessary.

The catalyst is preferably used by being supported on a support from the viewpoint of maintaining the activity for a long term. As the support, usually a porous substance is used, and in the material thereof, a carbon-based support is preferred. Examples of the carbon-based support include activated carbon and coconut shell charcoal, and coconut shell charcoal is preferred. The amount of the catalyst supported on the support is not particularly limited because the catalyst is effective even in a slight amount. From the viewpoint of maintaining the activity for a long term, the amount of the catalyst supported on the support is preferably about 0.1 to 0.5% by mass.

The amount of hydrogen in the catalytic hydrogenation treatment is preferably 2-fold mol or more based on 4CBA contained in the crude terephthalic acid solution. The time for performing the catalytic hydrogenation treatment should be time sufficient for the hydrogenation reaction to proceed substantially, and is generally in the range of 1 to 60 minutes, preferably 2 to 20 minutes. The catalytic hydrogenation is generally performed in a continuous scheme.

The crude terephthalic acid solution after the catalytic hydrogenation treatment is, for example, preferably filtered through a filter made of sintered titanium or another sintered metal or carbon particles in order to prevent the contamination of fine powders produced from the abrasion of the catalyst support used such as activated carbon.

[Step (c)]

The step (c) is the step of depressurizing and cooling a reaction liquid after the catalytic hydrogenation treatment in stages with two or more stages of crystallization vessels, to crystallize terephthalic acid to obtain a terephthalic acid slurry.

The reaction liquid after the catalytic hydrogenation is introduced into two or more stages of crystallization vessels coupled in series, and depressurized in stages, and thus cooled to 120 to 200° C. by the flash evaporation of water, and the terephthalic acid crystal crystallizes, and terephthalic acid crystal slurry is obtained.

The number of stages of the crystallization vessels coupled in series influences the average particle diameter and particle size distribution of the purified terephthalic acid crystal. Terephthalic acid crystals having a moderate average particle diameter and a narrow particle size distribution have a small heating load during drying and exhibit good behavior as a starting material of polyester. As the number of stages of crystallization vessels becomes larger, the amounts of impurities in the crystal can be decreased. Even if the number of stages of crystallization vessels is seven or more stages, the effect of decreasing impurities is small, and therefore the number of stages of crystallization vessels is preferably two to six stages, more preferably three to five stages.

The temperature of each crystallization vessel and the residence time in each crystallization vessel also influence the average particle diameter and particle size distribution of the purified terephthalic acid crystal, and the amounts of impurities in the crystal. Particularly, the temperature of the first-stage crystallization vessel (first crystallization vessel) and the residence time in the first-stage crystallization vessel have a large influence on the average particle diameter of the crystal. The temperature of the first crystallization vessel is preferably 230 to 270° C., more preferably 240 to 260° C. By setting the temperature of the first crystallization vessel at 230 to 270° C., a purified terephthalic acid crystal that has a small heating load during drying and contain small amounts of impurities can be obtained.

The residence time in the first crystallization vessel (hereinafter sometimes described as $T_1$) is 0.07 to 0.5 hr (hereinafter also referred to as a condition (1)), preferably 0.08 to 0.4 hr, and more preferably 0.1 to 0.3 hr. The average particle diameter of the purified terephthalic acid crystal tends to become larger as the residence time becomes longer. By setting $T_1$ at 0.07 to 0.5 hr, purified terephthalic acid crystals that have a moderate average particle diameter, have a small heating load during drying, and exhibit good behavior as a starting material of polyester are obtained.

The residence time in the second- and subsequent-stage crystallization vessels is preferably 0.08 to 0.5 hr, more preferably 0.1 to 0.4 hr. By setting the residence time in the second- and subsequent-stage crystallization vessels at 0.08 to 0.5 hr, purified terephthalic acid crystals that have a small heating load during drying and exhibit good behavior as a starting material of polyester can be obtained. The residence time in the second crystallization vessel (hereinafter sometimes described as $T_2$) also has a large influence on the average particle diameter and particle size distribution of the crystal, and therefore the total residence time of the residence time in the first crystallization vessel and the residence time in the second crystallization vessel, $T_1+T_2$ [hr], is preferably 0.15 to 0.7 hr.

For the temperature of the second- and subsequent-stage crystallization vessels, the temperature is preferably lowered in stages so that the temperature of the final crystallization vessel is 120 to 200° C., and specifically, the temperature is preferably set at temperature 20 to 40° C. lower than that in the previous stage per stage. By performing crystallization in stages with two or more stages of crystallization vessels, the terephthalic acid crystal slurry suitable for supply to the mother liquor replacement tower in the next step is obtained.

[Step (d)]

The step (d) is the step of introducing the terephthalic acid crystal slurry into an upper portion of a mother liquor replacement tower, bringing the terephthalic acid crystal into contact with an upward flow of replacement water introduced from a tower lower compartment of the mother liquor replacement tower while making the terephthalic acid crystal settled down in the tower, and withdrawing the terephthalic acid crystal as slurry with the replacement water from the tower lower compartment (hereinafter also referred to as a "mother liquor replacement step").

The temperature of the terephthalic acid crystal slurry introduced into the upper portion of the mother liquor replacement tower is preferably 120 to 200° C., more preferably 130 to 180° C., and further preferably 140 to 170° C. By setting the temperature of the terephthalic acid crystal slurry at 120 to 200° C., the contamination of impurities into the terephthalic acid crystal can be suppressed, and the amount of terephthalic acid dissolved in the mother liquor can be reduced.

In the mother liquor replacement step, the mother liquor containing many impurities in the supplied terephthalic acid crystal slurry (hereinafter also referred to as "starting slurry") is replaced by fresh water.

The apparatus used in the mother liquor replacement step (that is, a "mother liquor replacement tower") mainly comprises a tower upper compartment, a tower bottom compartment, and a tower middle part.

The tower upper compartment has an introduction portion for the starting slurry comprising the mother liquor containing the terephthalic acid crystal. The introduction portion for the starting slurry may open at the inner wall of the tower upper compartment, preferably extends and opens in the tower upper compartment from the viewpoint of making the dispersion of the crystal well. Further, the opening tip portion of the starting slurry introduction portion may be placed downward, and a mechanism for promoting the dispersion of the crystal, such as a dispersion plate, may be provided in the opening tip portion. The tower upper compartment further comprises a mother liquor discharge port, and the mother liquor comprising few terephthalic acid crystals is withdrawn from the mother liquor discharge port and introduced into a certain treatment chamber.

A structure such as a shelf plate to inhibit the movement of the terephthalic acid crystal settling by gravity need not be provided in the tower middle part.

The tower lower compartment comprises a replacement water supply portion, a withdrawing port for the purified terephthalic acid slurry obtained by replacement by the replacement water, portions for adjusting the replacement water supply flow rate and the replacement slurry withdrawing flow rate, and a stirring apparatus for the slurry in the tower lower compartment. The position of the withdrawing port for the purified terephthalic acid slurry obtained by replacement by the replacement water is preferably closer to the lower portion of the tower lower compartment because the slurry has high specific gravity.

The size of the mother liquor replacement tower can be appropriately changed in accordance with the throughput of the terephthalic acid crystal to be treated. The inner diameter of the tower middle part needs to be such an inner diameter that when the throughput of the terephthalic acid crystal subjected to the catalytic hydrogenation treatment is Q [ton/hr], and the tower cross-sectional area of the mother liquor replacement tower is A [m$^2$], $$0.3 \leq A/Q \leq 0.8$$

holds (hereinafter also referred to as a condition (2)). Further, the inner diameter of the tower middle part is preferably such an inner diameter that $$0.35 \leq A/Q \leq 0.6$$

holds.

In the case of an inner diameter that sets A/Q smaller than 0.3, the separation of the mother liquor and the terephthalic acid crystal is insufficient, and the amounts of impurities in the purified terephthalic acid increase. In addition, in some cases, an outflow of the terephthalic acid crystal from the mother liquor withdrawing portion of the tower upper compartment occurs. On the other hand, in the case of an inner diameter that sets A/Q larger than 0.8, the amount of the mother liquor mixed into the tower lower compartment increases due to the large tower cross-sectional area, and therefore the amounts of impurities in the purified terephthalic acid increase.

The diameters of the tower upper compartment and the tower lower compartment should be diameters at the same level as the tower middle part, and can also be larger diameters.

The height of the tower is preferably a height at which the supplied terephthalic acid crystal disperses in the entire interior of the tower, and specifically, preferably such a height that the distance from the starting slurry introduction portion to the tower bottom is one to three times the tower inner diameter.

The mother liquor replacement effect in the mother liquor replacement tower is influenced not only by the tower inner diameter but by the average particle diameter and particle size distribution of the terephthalic acid crystal to be treated. Therefore, the mother liquor replacement effect fluctuates in accordance with the residence time in the first crystallization vessel, $T_1$, which has a large influence on the average particle diameter and particle size distribution of the terephthalic acid crystal. In order to maintain a high mother liquor replacement effect, $T_1 \times A/Q$ needs to satisfy the condition of the following formula (also referred to as a condition (3)).

$$0.035 \leq T_1 \times A/Q \leq 0.25$$

$T_1 \times A/Q$ preferably satisfies the condition of the following formula.

$$0.04 \leq T_1 \times A/Q \leq 0.2$$

$T_1 \times A/Q$ more preferably satisfies the condition of the following formula.

$$0.045 \leq T_1 \times A/Q \leq 0.15$$

By setting $T_1 \times A/Q$ at 0.035 to 0.25, the high mother liquor replacement effect can be obtained. When $T_1 \times A/Q$ is smaller than 0.035, the mother liquor replacement effect decreases. When $T_1 \times A/Q$ is larger than 0.25, the mother liquor replacement effect decreases, and oversize crystallization vessels and an oversize mother liquor replacement tower are necessary.

A specific example of a method for operating the mother liquor replacement tower will be described.

The terephthalic acid slurry introduced from the tower upper compartment forms a layer having high slurry concentration in the mother liquor replacement tower lower compartment by settling by gravity, and an interface is formed between the high slurry concentration layer and the low slurry concentration region where the terephthalic acid crystal settle by gravity.

Fluidity is preferably provided to the slurry layer in the tower lower compartment by the stirring apparatus in order to prevent the consolidation of the crystal and clogging. When stirring is performed more than necessary, the impurities to be replaced is also uniformly stirred, and the replacement efficiency decreases significantly. Therefore, moderate stirring to the extent that the fluidity of the slurry layer is not impaired is preferred. As the power of the stirrer, the power per unit volume of the slurry layer in the tower lower compartment is preferably 0.05 to 1.0 kWh/m$^3$, more preferably 0.1 to 0.8 kWh/m$^3$, and further preferably 0.2 to 0.7 kWh/m$^3$.

With an upward flow of replacement water introduced from the tower lower portion, mainly the mother liquor is withdrawn from the tower top portion. The fine crystal in the supplied terephthalic acid slurry rises with the upward flow without settling, and is withdrawn from the tower top portion together with the mother liquor. Therefore, in the high-purity terephthalic acid produced through the mother liquor replacement apparatus, the proportion of small particle diameter of 53 μm or less is small, and the proportion of fine particle diameter of 38 μm or less is particularly small.

By setting the residence time in the first crystallization vessel, $T_1$, in the crystallization step and the cross-sectional area of the mother liquor replacement tower to satisfy the conditions (1) to (3), the proportion of the crystal having the small particle diameter can be further decreased, and high-purity terephthalic acid in which the proportion of the crystal having the small particle diameter of less than 53 μm is 15% or less, and the proportion of the crystal having the fine particle diameter of less than 38 μm is 7% or less can be obtained. In this application, the proportion of the particle diameter of the crystal indicates a proportion obtained by classification by the sieving of crystals.

The linear velocity of the upward liquid flow of the replacement water in the mother liquor replacement tower middle part is preferably 0.2 to 1.5 m/hr (based on the empty tower), more preferably 0.5 to 1.0 m/hr. When the linear velocity is too low, the separation of the mother liquor and the terephthalic acid crystal is insufficient, and the amounts of impurities in the purified terephthalic acid increase. In addition, when the linear velocity is too low, the fine crystal of terephthalic acid rising with the mother liquor withdrawn from the tower top portion decreases. On the other hand, when the linear velocity is too high, a disadvantage is that the amount of the replacement water used increases.

Here, the linear velocity of the upward liquid flow of the replacement water can be calculated from the balance of water between the amount of the replacement water supplied and the withdrawn slurry from the tower bottom.

The pressure of the mother liquor replacement tower is the pressure at which at least the temperatures of the starting slurry and the replacement water can be maintained. For the upper limit of the pressure, there are no operational restrictions, but operating at excessive pressure requires increasing the pressure resistance of the replacement tower and therefore causes an increase in apparatus cost. The pressure of the mother liquor replacement tower is preferably 0.1 to 2 MPa (gauge pressure), more preferably 0.2 to 1.5 MPa.

[Step (e)]

The step (e) is the step of subjecting the slurry withdrawn from the tower lower compartment to solid-liquid separation into water and the terephthalic acid crystal, and drying the separated terephthalic acid crystal.

The slurry withdrawn from the mother liquor replacement tower lower compartment is separated into terephthalic acid crystal and water by a solid-liquid separation apparatus such as a rotary vacuum filter. The terephthalic acid crystal obtained by the solid-liquid separation are obtained as a cake, and the water content of the cake after the solid-liquid separation is 12 to 13% by mass. Namely, the water content of the cake can be easily set at 15% by mass or less only in the solid-liquid separation step by the production method in the present embodiment. Since the water content of the cake is low, the energy consumption in the following drying step can be reduced. In the next drying step, a steam tube dryer or the like usually used for terephthalic acid production can be used, and further, since the water content of the terephthalic acid cake is low, the cake after the separation can be directly dried using a fluidized bed dryer.

In the high-purity terephthalic acid produced in the present embodiment, the particle size distribution is narrow, the proportion of the crystal having particle the diameter of less than 53 μm is decreased to 15% or less, and the proportion of the crystal having the particle diameter of 212 μm or more is also decreased to 15% or less.

One of the present embodiment is high-purity terephthalic acid in which the median diameter is 100 to 130 μm, and to the mass of all crystals, the proportion of the crystal of less than 53 μm is 15% by mass or less, and the proportion of the crystal having the particle diameter of 212 μm or more is 15% by mass or less. High-purity terephthalic acid in which the median diameter is 100 to 130 μm, and to the mass of all crystals, the proportion of the crystal having the particle diameter of 53 μm or less is 15% by mass or less, and the proportion of the crystal having the particle diameter of 212 μm or more is 15% by mass or less can be produced by the production method in the present embodiment.

The proportion of the crystal having the particle diameter of 212 μm or more in the high-purity terephthalic acid in the present embodiment is preferably 12% or less.

In the high-purity terephthalic acid in the present embodiment, the proportion of the crystal having the particle diameter of less than 38 μm is preferably 7% or less.

When the proportion of the crystal having the particle diameter of 212 μm or more is 15% by mass or less, good behavior as a starting material of polyester can be exhibited.

When the proportion of the crystal of less than 53 μm is 15% by mass or less, the heating load in solid-liquid separation and drying can be made small.

EXAMPLES

Next, the present invention will be more specifically described by Examples. However, the present invention is not limited by these Examples.

The mother liquor replacement effect (hereinafter also referred to as a mother liquor replacement rate) in the following Examples was calculated according to the following formula.

the mother liquor replacement rate (%)=(the amount of benzoic acid contained in a mother liquor withdrawn from the mother liquor discharge port of a tower upper compartment)/(the amount of benzoic acid contained as an impurity in the crude terephthalic acid slurry)×100

The terephthalic acid content (% by mass) in a mother liquor withdrawn from the upper compartment of the mother liquor replacement tower was calculated from the weight of crystals obtained by filtering the mother liquor cooled to ordinary temperature through a filter.

Example 1

The liquid-phase oxidation reaction of p-xylene was performed in an acetic acid solution using cobalt and manganese catalysts and a promoter of a bromide compound, followed by crystallization and cooling. The precipitated crude terephthalic acid crystals were separated. The obtained crude terephthalic acid was mixed with water and heated and dissolved, and the solution was subjected to a catalytic hydrogenation reaction at 281° C. using the hydrogenation reaction vessel 1 in FIG. 1. The solution of terephthalic acid that was the reaction liquid was fed to the first crystallization vessel of crystallization vessels 2 at a flow rate of 126 tons per hour (the terephthalic acid content was 24.8% by mass, and the terephthalic acid crystal throughput Q was 31.3 tons per hour) to produce a crystallization slurry at 250° C. At this time, the slurry residence time in the first crystallization vessel calculated from the liquid level in the first crystallization vessel was 0.12 hr. This crystallization slurry at 250° C. was continuously supplied to the second crystallization vessel at 230° C. through transfer piping at a flow rate of 114 tons per hour (the terephthalic acid content was 27.4% by mass). At this time, the slurry residence time in the second crystallization vessel was 0.20 hr. Further, the crystallization slurry was continuously supplied to the third crystallization vessel at about 195° C. at a flow rate of 111 tons per hour (the terephthalic acid content was 28.2% by mass). Further, the crystallization slurry was continuously supplied to the fourth crystallization vessel at 165° C. at a flow rate of 104 tons per hour (the terephthalic acid content was 30.1% by mass). The slurry residence times in the third crystallization vessel and the fourth crystallization vessel were both 0.20 hr.

The terephthalic acid slurry at 165° C. obtained from the fourth crystallization vessel was introduced into a mother liquor replacement tower 4 having a tower inner diameter of 4 m and a tower cross-sectional area of 12.6 m² through a starting slurry introduction nozzle 5 at a flow rate of 100 tons per hour (the terephthalic acid content was 31.3% by mass) using a starting slurry supply pump 3. Replacement water at 100° C. was introduced into the mother liquor replacement tower 4 through a replacement water introduction port 9 by a replacement water supply pump 8 at a flow rate of 66 tons per hour. With the introduced terephthalic acid slurry, by settling by gravity, a deposited layer of terephthalic acid crystals "b" having high slurry concentration was formed in the lower portion of the mother liquor replacement tower 4, forming an interface with the portion having low slurry concentration (also referred to as a deposited layer upper surface) "a". With an upward flow of the replacement water supplied from the replacement water introduction port, the fine terephthalic acid crystals that did not completely settle were withdrawn from a mother liquor discharge port 6 together with the mother liquor at a flow rate of 74 tons per hour (the terephthalic acid content was 0.11% by mass). The purified terephthalic acid slurry was withdrawn from purified terephthalic acid slurry-withdrawing-port 7 in the lower portion of the mother liquor replacement tower 4 at a flow rate of 92 tons per hour (the terephthalic acid content was 33.9% by mass).

The terephthalic acid slurry at temperature of 110° C. was withdrawn from the purified terephthalic acid slurry-withdrawing-port 7 and fed to a crystallization vessel 10 to produce slurry at 100° C. The obtained slurry was fed to a rotary vacuum filter at a flow rate of 95 tons per hour (the terephthalic acid content was 32.8% by mass) and subjected to solid-liquid separation from water. The wet cake of the purified terephthalic acid before being fed to a drying step was sampled.

The sampled wet cake was dried in a dryer purged with nitrogen at 120° C. for 9 hours, and the water content was calculated from the weight before and after the drying. The amount of water in the wet cake was calculated as a mass percentage and, as a result, was 12.4% by mass.

The purified terephthalic acid crystals after drying obtained in Example 1 were sieved and classified using Robot Sifter manufactured by Seishin Enterprise Co., Ltd. The proportion of the crystal of 38 μm or less was 5.18% by mass. The median diameter was 116 μm.

The operation conditions, the mother liquor replacement rate, the terephthalic acid concentration in the mother liquor discharge port, the water content of the wet cake on the vacuum filter, and the particle diameter distribution of the dry crystals in Example 1 are shown in Table 1.

Examples 2 to 5 and Comparative Examples 1 to 3

The purification of crude terephthalic acid was performed using the apparatus used in Example 1. The apparatus was operated with the terephthalic acid throughput Q and the liquid levels in the first crystallization vessel and the second crystallization vessel adjusted and the crystallization vessel residence times T1 and T2, A/Q, and $T_1 \times A/Q$ changed. The flow rates of water for crude terephthalic acid purification and replacement water were flow rates proportional to the terephthalic acid throughput Q so that the slurry concentration was the same as Example 1, and the slurry flow rate in each portion was also adjusted in accordance with the terephthalic acid throughput Q. The operation was performed with the temperatures of the hydrogenation reaction vessel, each crystallization vessel, and the mother liquor replacement tower, and the residence times in the third crystallization vessel and the fourth crystallization vessel being the same as Example 1.

The operation conditions, the mother liquor replacement rate, the terephthalic acid concentration in the mother liquor discharge port, the water content of the wet cake, and the particle diameter distribution of the dry crystals in each Example and Comparative Example are shown in Table 1.

Comparative Example 4

The purification of crude terephthalic acid was performed in the apparatus used in Example 1 by a method of directly supplying the slurry in the fourth crystallization vessel to the crystallization vessel 10 without using the mother liquor replacement tower. Operation was performed with the temperature of each portion being the same as Example 1, except that the temperature of the fourth crystallization vessel was 155° C., and the residence time in each crystallization vessel being the same as Example 2.

The operation conditions, the mother liquor replacement rate, the terephthalic acid concentration in the mother liquor discharge port, the water content of the wet cake, and the particle diameter distribution of the dry crystals are shown in Table 1.

TABLE 1

| | | Example 1 | Example 2 | Example 3 | Example 4 | Example 5 | Comparative Example 1 | Comparative Example 2 | Comparative Example 3 | Comparative Example 4 |
|---|---|---|---|---|---|---|---|---|---|---|
| [Operation conditions] | | | | | | | | | | |
| Terephthalic acid throughput Q | (ton/hr) | 31.3 | 31.3 | 20.2 | 36.7 | 20.3 | 44.8 | 20.2 | 36.6 | 31.2 |
| A/Q | (m²·hr/ton) | 0.40 | 0.40 | 0.62 | 0.34 | 0.62 | 0.28 | 0.62 | 0.34 | — |
| First crystallization vessel residence time $T_1$ | (hr) | 0.12 | 0.20 | 0.25 | 0.20 | 0.10 | 0.20 | 0.06 | 0.10 | 0.2 |
| Second crystallization vessel residence time $T_2$ | (hr) | 0.17 | 0.20 | 0.28 | 0.20 | 0.20 | 0.20 | 0.08 | 0.20 | 0.2 |
| $T_1 \times A/Q$ | (m²·hr²/ton) | 0.048 | 0.081 | 0.156 | 0.069 | 0.062 | 0.056 | 0.037 | 0.034 | — |

TABLE 1-continued

|  |  | Example 1 | Example 2 | Example 3 | Example 4 | Example 5 | Comparative Example 1 | Comparative Example 2 | Comparative Example 3 | Comparative Example 4 |
|---|---|---|---|---|---|---|---|---|---|---|
| [Results] | | | | | | | | | | |
| Mother liquor replacement rate | (%) | 94.3 | 96.1 | 93.6 | 91.8 | 93.2 | 78.5 | 86.5 | 83.1 | — |
| Terephthalic acid concentration in mother liquor discharge port | (% by mass) | 0.11 | 0.10 | 0.08 | 0.17 | 0.14 | 1.2 | 0.6 | 0.3 | — |
| Wet cake water content | (% by mass) | 12.4 | 12.8 | 13.8 | 12.9 | 13.4 | 13.1 | 16.5 | 14.7 | 15.2 |
| Dry crystal median diameter | (μm) | 112 | 118 | 127 | 116 | 111 | 119 | 90 | 109 | 108 |
| Particle diameter distribution (cumulative mass %) | 250 μm or more | 3.5 | 5.3 | 7.5 | 4.5 | 3.7 | 5.0 | 2.4 | 4.1 | 3.0 |
| | 212 μm or more | 9.8 | 13.4 | 14.9 | 11.8 | 10.6 | 12.7 | 6.1 | 10.9 | 9.9 |
| | 180 μm or more | 17.0 | 21.4 | 24.9 | 19.4 | 17.8 | 21.0 | 12.3 | 18.1 | 18.3 |
| | 150 μm or more | 30.2 | 34.1 | 38.6 | 32.4 | 31.1 | 34.5 | 21.9 | 29.4 | 28.9 |
| | 125 μm or more | 41.8 | 46.2 | 50.9 | 44.5 | 41.7 | 46.7 | 30.9 | 40.7 | 40.6 |
| | 90 μm or more | 64.2 | 66.7 | 70.5 | 67.5 | 64.0 | 67.7 | 50.2 | 62.2 | 60.3 |
| | 53 μm or more | 87.3 | 88.1 | 90.2 | 88.3 | 86.9 | 89.1 | 78.0 | 84.8 | 81.2 |
| | 38 μm or more | 95.1 | 94.9 | 95.3 | 96.4 | 95.7 | 94.9 | 90.6 | 94.3 | 90.4 |

In Comparative Example 1 in which the terephthalic acid throughput Q is high and A/Q is too small, the mother liquor replacement rate decreases significantly. In Comparative Example 2 in which the residence time in the first crystallization vessel, $T_1$, is too short, the crystal particle diameters are small, and a decrease in the mother liquor replacement rate is noted. In Comparative Example 3 in which $T_1 \times A/Q$ is too small, the particle diameters of the crystals are small, and the mother liquor replacement rate deteriorates greatly, compared with Example 4 in which the terephthalic acid throughput Q is equal. In Comparative Example 4 in which the mother liquor replacement tower is not used, the ratios of fine crystals of less than 53 μm and less than 38 μm are high, and the water content of the wet cake on the solid-liquid separator is high.

This application is based on a Japanese Patent Application (Japanese Patent Application No. 2016-179404) filed on Sep. 14, 2016, the contents of which are incorporated herein by reference.

INDUSTRIAL APPLICABILITY

The production method of the present invention has industrial applicability in the field of terephthalic acid production. In addition, the terephthalic acid of the present invention can be used as a starting material of polyester and has industrial applicability in polyester production.

REFERENCE SIGNS LIST

1: hydrogenation reaction vessel
2: crystallization vessel
3: starting slurry supply pump
4: mother liquor replacement tower
5: starting slurry introduction nozzle
6: mother liquor discharge port
7: purified terephthalic acid slurry-withdrawing-port
8: replacement water supply pump
9: replacement water introduction port
10: crystallization vessel
a: deposited layer upper surface
b: deposited layer of terephthalic acid crystal

The invention claimed is:

1. A method for producing a high-purity terephthalic acid, the method comprising:
   (a) liquid-phase oxidizing a p-phenylene compound to obtain crude terephthalic acid crystals;
   (b) dissolving the crude terephthalic acid crystals in water and to obtain a mixture, and then subjecting the mixture to catalytic hydrogenation treatment obtain a reaction liquid;
   (c) depressurizing and cooling the reaction liquid after the catalytic hydrogenation treatment in stages with two or more stages of crystallization vessels, to crystallize terephthalic acid and obtain a terephthalic acid slurry containing crystallized terephthalic acid;
   (d) introducing the terephthalic acid slurry into an upper portion of a mother liquor replacement tower, bringing the crystallized terephthalic acid into contact with an upward flow of replacement water introduced from a tower bottom portion of the mother liquor replacement tower while making the crystallized terephthalic acid settle down in the tower, and withdrawing the crystallized terephthalic acid as a withdrawn slurry with the replacement water from a tower lower compartment; and
   (e) performing solid-liquid separation of the withdrawn slurry into water and separated terephthalic acid crystals, and drying the separated terephthalic acid crystals,
   wherein, when a throughput of the crude terephthalic acid crystals subjected to the catalytic hydrogenation treatment is Q [ton/hr], and a residence time in a first-stage crystallization vessel of the two or more stages of crystallization vessels is $T_1$ [hr], and a cross-sectional area of the mother liquor replacement tower is A [m$^2$], following conditions (1) to (3) are all satisfied:

$$0.07 \leq T_1 \leq 0.5 \quad (1)$$

$$0.3 \leq A/Q \leq 0.8 \quad (2)$$

$$0.035 \leq T_1 \times A/Q \leq 0.25 \quad (3).$$

2. The production method according to claim 1, wherein a number of stages of the two or more stages of crystallization vessels is three to five stages.

3. A high-purity terephthalic acid, wherein:
  a median diameter of the high-purity terephthalic acid is 100 to 130 μm;
  proportion of crystals having particle diameters of less than 53 μm in the high-purity terephthalic acid is 15% or less; and
  a proportion of crystals having particle diameters of 212 μm or more in the high-purity terephthalic acid is 15% or less.

4. The high-purity terephthalic acid according to claim 3, wherein a proportion of crystals having particle diameters of less than 38 μm in the high-purity terephthalic acid is 7% or less.

\* \* \* \* \*